(12) United States Patent
Gordon et al.

(10) Patent No.: US 12,256,961 B2
(45) Date of Patent: Mar. 25, 2025

(54) SCOLIOSIS CORRECTION SYSTEMS, METHODS, AND INSTRUMENTS

(71) Applicant: GLOBUS MEDICAL, INC., Audubon, PA (US)

(72) Inventors: Jeffrey David Gordon, Phoenixville, PA (US); John LaColla, West Chester, PA (US)

(73) Assignee: Globus Medical, Inc., Audubon, PA (US)

( * ) Notice: Subject to any disclaimer, the term of this patent is extended or adjusted under 35 U.S.C. 154(b) by 339 days.

(21) Appl. No.: 17/657,204

(22) Filed: Mar. 30, 2022

(65) Prior Publication Data
US 2022/0330987 A1 Oct. 20, 2022

Related U.S. Application Data

(63) Continuation of application No. 17/242,481, filed on Apr. 28, 2021, now Pat. No. 12,121,266, which is a continuation of application No. 16/284,394, filed on Feb. 25, 2019, now Pat. No. 11,020,149.

(60) Provisional application No. 62/636,212, filed on Feb. 28, 2018.

(51) Int. Cl.
*A61B 17/88* (2006.01)
*A61B 17/70* (2006.01)
*A61B 5/00* (2006.01)
*A61F 2/46* (2006.01)

(52) U.S. Cl.
CPC ...... *A61B 17/7019* (2013.01); *A61B 17/7049* (2013.01); *A61B 5/4566* (2013.01); *A61B 17/7044* (2013.01); *A61B 17/7053* (2013.01); *A61F 2/4611* (2013.01)

(58) Field of Classification Search
CPC ......... A61B 17/7019–7031; A61B 17/82–826; A61B 17/88; A61B 17/8869
See application file for complete search history.

(56) References Cited

U.S. PATENT DOCUMENTS

| | | | |
|---|---|---|---|
| 10,022,159 B2 * | 7/2018 | Simpson | A61B 17/8869 |
| 2002/0072753 A1 * | 6/2002 | Cohen | A61B 17/8861 606/103 |
| 2003/0083657 A1 * | 5/2003 | Drewry | A61B 17/7031 606/328 |
| 2004/0138666 A1 * | 7/2004 | Molz, IV | A61B 17/8869 606/103 |
| 2006/0167464 A1 * | 7/2006 | Allen | A61B 17/8869 606/103 |
| 2006/0217715 A1 * | 9/2006 | Serhan | A61B 17/7053 606/86 A |
| 2008/0262551 A1 * | 10/2008 | Rice | A61B 17/8869 606/267 |
| 2009/0082776 A1 * | 3/2009 | Cresina | A61B 17/8861 606/103 |

(Continued)

*Primary Examiner* — Eduardo C Robert
*Assistant Examiner* — Michelle C Green (57) ABSTRACT

Devices, systems and methods for use in spinal surgeries. The system may include a fastener system comprising a fastener, a staple, and a locking cap. A cord may extend along the spine and through at least one fastener system. An instrument may be provided for tensioning the cord. The system may, for example, apply fixation on the convexity of the scoliotic vertebrae to limit growth on the convex side and allow unilateral growth on the concave side.

18 Claims, 6 Drawing Sheets

(56) References Cited

U.S. PATENT DOCUMENTS

| | | | | |
|---|---|---|---|---|
| 2012/0232533 A1* | 9/2012 | Veldman | ............ | A61B 17/8869 |
| | | | | 606/1 |
| 2016/0000468 A1* | 1/2016 | Samdani | ............ | A61B 17/7079 |
| | | | | 606/279 |
| 2018/0185080 A1* | 7/2018 | Bosshard | ............ | A61B 17/8861 |
| 2018/0353217 A1* | 12/2018 | Rice | ................... | A61B 17/8869 |
| 2019/0059949 A1* | 2/2019 | Ziemek | ................ | A61B 17/809 |
| 2019/0059958 A1* | 2/2019 | Mast | ................. | A61B 17/7022 |

* cited by examiner

SCOLIOSIS CORRECTION SYSTEMS, METHODS, AND INSTRUMENTS

CROSS-REFERENCE TO RELATED APPLICATION

This application is a continuation of U.S. patent application Ser. No. 17/242,481 filed on Apr. 28, 2021, which is a continuation of U.S. patent application Ser. No. 16/284,394 filed on Feb. 25, 2019, which claims priority to U.S. Provisional Application No. 62/636,212, filed Feb. 28, 2018, all of which are incorporated by reference herein in their entirety for all purposes.

FIELD

The present disclosure provides devices, systems, and instruments for use in spinal surgeries.

BACKGROUND

The vertebrate spine is the axis of the skeleton providing structural support for the other parts of the body. Scoliosis is a term used to describe any abnormal, sideway curvature of the spine. The most common form of scoliosis for patients between the age of 10 and 18 years is termed adolescent idiopathic scoliosis (AIS). Although the particular cause of this type of scoliosis is still unknown, advancements in the medical field have enabled doctors to increase the likelihood of successfully treating scoliosis.

One type of spinal surgery for treating scoliosis is the use of implantable rods. One or more rods are implanted into the patient through the back of the spine. The rods may be secured to the spine to correct the condition. There remains a need for improved systems that facilitate scoliosis correction and serve as a means for deformity correction with or without fusion.

SUMMARY

To meet this and other needs, scoliosis correction devices, systems, methods, and instruments are provided. The systems offer implants and instruments for deformity correction with or without fusion. Traditional rods or a flexible, durable, biocompatible cord may be secured to the spine. The system may apply fixation on the convexity of the scoliotic vertebrae to limit growth on the convex side and allow unilateral growth on the concave side. The system creates an optimized construct for spinal alignment to maintain stability while allowing growth in skeletally immature patients. In addition, the instruments facilitate rod or cord insertion and/or tensioning, for example, using an anterior or posterior approach.

According to one embodiment, a spinal system includes a fastener system comprising a fastener, a staple, and a locking cap. The fastener has a threaded portion and a head portion configured to move relative to the threaded portion. The staple includes a ring configured to surround the threaded portion of the fastener and a plurality of prongs configured to engage bone. A rod or cord may be provided in the system and is configured to be retained within one or more of the fastener systems. The rod or cord may be tensioned to impart a compressive force to the scoliotic vertebrae.

According to another embodiment, a spinal system includes a first fastener system, a second fastener system, and a cord. The first fastener system includes a first fastener, a first staple, and a first locking cap. The first fastener has a first threaded portion and a first head portion configured to move relative to the first threaded portion. The first staple includes a first ring configured to surround the first threaded portion of the first fastener and a first plurality of prongs configured to engage bone. The second fastener system includes a second fastener, a second staple, and a second locking cap. The second fastener has a second threaded portion and a second head portion configured to move relative to the second threaded portion. The second staple includes a second ring configured to surround the second threaded portion of the second fastener and a second plurality of prongs configured to engage bone. The cord extends between at least the first fastener system and the second fastener system. The cord is tensioned between the first fastener system and the second fastener system, for example, to correct a curve of the spine.

According to another embodiment, an instrument for tensioning the cord includes a body having an opening. The opening receives a compressor tube, and the compressor tube receives a threaded shaft therethrough. The cord is configured to be affixed to a distal end of the threaded shaft. Movement of the threaded shaft applies a compressive force to the cord to tension the cord within the fastener system.

According to yet another embodiment, an instrument for tensioning the cord may include a first portion and a second portion coupled to the first portion at a pivot point, thereby pivotally connecting the first and second portions together. The first portion includes a first tubular member and the second portion includes a second tubular member. The first and second tubular members are aligned along a common axis such that the opening is a central longitudinal opening extending through the first and second tubular members. In a second position, the first and second tubular members are not aligned along the common axis and are angled relative to one another. The first portion includes a first handle portion extending from the first tubular member and the second portion includes a second handle portion extending from the second tubular member. Distal ends of the first and second handle portions may be connected with a ratchet. The ratchet may extend from the distal end of the second handle portion at a pivot, and the ratchet is engagable with a pawl on the first handle portion. The ratchet may include a plurality of uni-directional teeth. The instrument may include a force gauge and a plurality of indicia, and when the force gauge moves, the plurality of indicia indicate the amount of compressive force on the cord and provided by the instrument.

According to yet another embodiment, an instrument for tensioning the cord includes a first, main handle that grasps the compressor tube and the threaded shaft. The instrument may include a second handle (e.g., a T-handle) or a knob. When using two handles, the two handles may be pulled apart from one another to impart the compressive forces on the cord. As an alternative to the T-handle, a knob may be used. The knob may have an internal thread to threadedly engage the threaded shaft. The knob may be turned to apply the compressive force to the cord.

According to yet another embodiment, a method of installing the system may include inserting one or more staples into an anterior aspect of each vertebral body. After the staple is fully seated against the vertebral body, the fastener may be inserted through the opening in the staple. Once the fasteners are placed, the cord may be selected and positioned within the heads of each fastener. The non-threaded locking caps may be installed in the heads of the fasteners. The cord is tensioned, for example, with the one or more instruments described herein, and after final tensioning of the cord, the locking caps are fully tightened to maintain the tension on the cord.

According to yet another embodiment, a kit includes one or more of the components, implants, instruments, or systems described herein. For example, the kit may include a plurality of fastener systems, for example, of different sizes, cords and/or rods, and one or more instruments including instruments for inserting and/or tensioning the cord.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Embodiments of the disclosure are generally directed to scoliosis correction devices, systems, methods of use, and instruments for installing the same. The scoliosis correction system may be used to apply fixation on the convexity of the scoliotic vertebrae. A rod or flexible cord, for example, may be used to limit growth on the convex side and allow unilateral growth on the concave side of the spine.

Figures 1, 2:
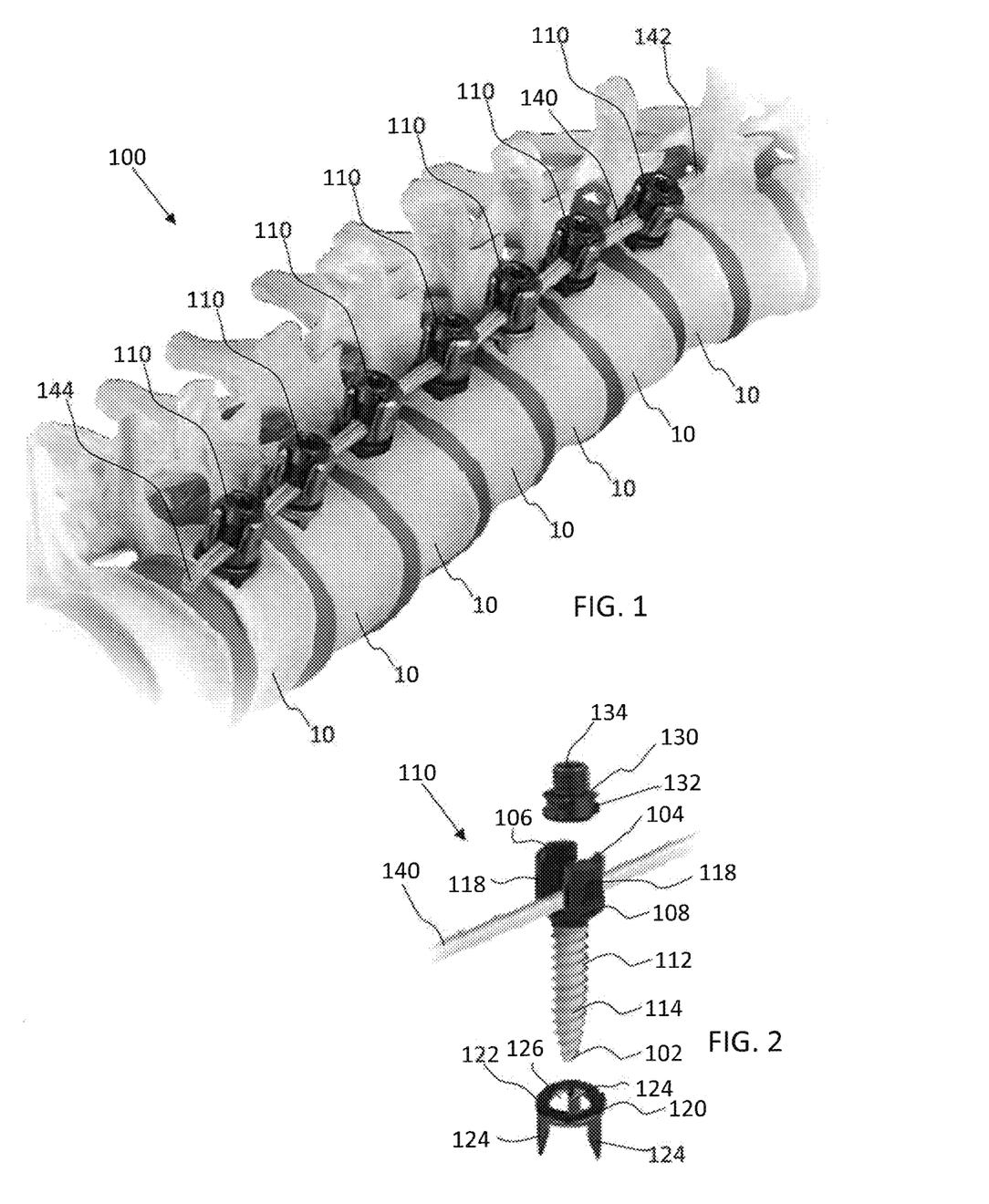
FIG. 1 is a perspective view of a spine with a spinal system according to one embodiment.
FIG. 2 is a perspective, exploded view of a fastener system for use with the spinal system of FIG. 1.
Figure 3:
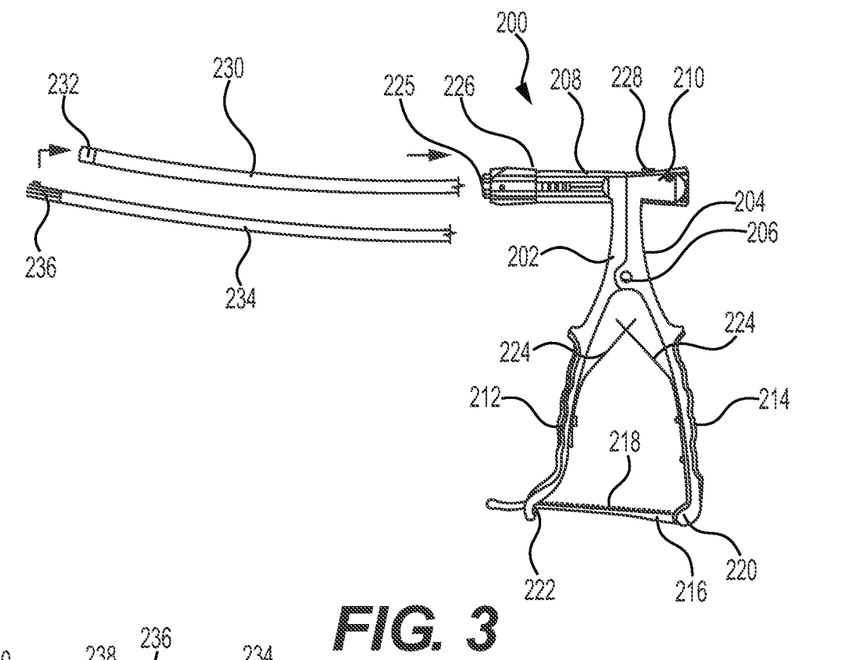
FIG. 3 is an exploded view of instrument for use with inserting and/or tensioning a cord within the spinal system of FIG. 1.

Referring now to FIG. 1, a scoliosis correction system 100 may include one or more fastener systems 110 secured to bone or vertebrae 10. The fastener systems 110 may be attached to an anterior aspect of each of the vertebral bodies 10, for example, adjacent to the rib head. Although seven fastener systems 110 are exemplified in the system 100 shown in FIG. 1, it will be appreciated that the surgeon could select any suitable number of fastener systems 110 as the surgeon deems appropriate to correct the deformity. The one or more fastener systems 110 are configured to retain a traditional rod or a cord 140 extending from a first end 142 to a second end 144. The rod or cord 140 is configured to be retained within the fastener systems 110 and tensioned to intraoperatively correct the deformity of the spine. The scoliosis correction system 100 may be implanted using an anterior or posterior spinal approach, for example. In particular, the system 100 may be implanted through a thoracoscopic approach or a mini-open thoracotomy to help minimize tissue disruption and/or scar tissue formation. The tensioned rod or cord 140 may provide for spinal alignment to maintain stability while allowing growth in skeletally immature patients.

The cord 140 may be a cable, wire, band, flexible or elastic member, for example. In one embodiment, the cord 140 is a narrow, flexible band. In some embodiments, the cord 140 is between 250-800 mm in length, for example, or may be cut to length, but any suitable length may be selected based on the deformity being corrected. As shown, the cord 140 is a single continuous cord extending from the first end 142 to the second 144, but it is also envisioned that more than one cord may be used or a section thereof may be coupled to another cord, rod, or other device, if desired. In some embodiments, the cord 140 is composed of a polymer, such as polyethylene terephthalate (PET), but any suitable biocompatible material may be selected. Preferably, the cord 140 is able to be placed under tension to achieve the proper amount of correction to the spine without fusion.

Turning to FIG. 2, the fastener system 110 may include a fastener 112, a staple 120, and a locking cap 130. The fastener 112 may extend from a distal end 102 to a proximal end 104. The distal end 102 may be configured to be received with the bone 10, and the proximal end 104 may be configured to sit above the bone 10. The fastener 112 may include a shaft portion or a threaded portion 114 and a yoke, tulip, or head portion 116. The threaded portion 114 may terminate at the distal end 102, for example, as a point, tapered to a narrowed end, or a blunt tip to facilitate insertion in the bone 10. In one embodiment, the distal end 102 may form a blunt tip for safe bicortical purchase in the bone 10. The threaded portion 114 may include any suitable type of threading. In one embodiment, the thread includes a double lead thread for rapid insertion, for example.

The yoke, tulip, or head portion 116 may be configured to move relative to the threaded portion 114. In one embodiment, the head portion 116 may be able to pivot about a longitudinal axis defined by the shaft portion of the fastener 112, thereby allowing for monoaxial movement of the head portion 116 relative to the threaded portion 114. In another embodiment, the head portion 116 may be able to move in a polyaxial manner relative to the threaded portion 114. It is also envisioned that the head portion 116 may be fixed relative to the threaded portion 114.

The head portion 116 of the fastener 112 may be in the form of a yoke or tulip defining a bore 106 therethrough, a body 108, and arms 118 that extend upwardly from the body 108. As shown in FIG. 2, the arms 118 may define a U-shaped channel sized to receive rod or cord 140. Each of the arms 118 has an interior surface configured to engage with the locking cap 130. Each of the arms 118 may also include an outer surface which defines a tool engagement groove for holding the head portion 116 with a suitable tool (not illustrated).

The locking cap 130 may be formed of two parts: an outer portion 132 and an inner portion 134. The outer portion 132 may define an opening therethrough for receiving the inner portion 132. The outer portion 132 may provide a non-threaded interface with the head portion 116 of the fastener 112. The inner portion 132 may be threaded to engage with interior threads within the outer portion 132. One or more features of the head portion 116 and locking cap 130 may be similar to those described in U.S. Pat. No. 8,888,827, which is incorporated by reference herein in its entirety for all purposes.

The fastener system 110 may further include a staple 120. The staple 120 may be formed of a ring 122 defining an opening 126. The ring 122 may be configured to surround the threaded portion 114 of the fastener 112 and a plurality of prongs 124 may extend from the ring 122 and are configured to engage the bone 10. In the embodiment shown, the ring 122 is a continuous ring, but it may also be split or otherwise shaped. In addition, the embodiment shown provides for three prongs 124 extending downwardly from the ring 122 and toward the distal end 102 of the fastener 112. The prongs 124 may help to increase the vertebral body fixation and/or increase resistance to screw toggle. Although three prongs 124 are exemplified, it will be appreciated that a different number or orientation of the prongs 124 may be selected.

The system 100 or components thereof may be comprised of any suitable biocompatible materials. For example, the staples 120, fasteners 112, and locking caps 130 may be manufactured from various biocompatible materials, such as metals, polymers, ceramics or combinations thereof. Exemplary materials include titanium (and titanium alloys), cobalt-chrome, stainless steel, and/or polyetheretherketone (PEEK), for example. In one embodiment, the fastener 112 (e.g., the threaded portion 114) is coated with a hydroxyapatite (HA) coating, which may help to promote bony ongrowth.

When installing the system 100, the one or more staples 120 may be inserted first or in tandem with the fastener 112. In one embodiment, the staples 120 may be positioned on the anterior aspect of the vertebral body 10. After the staple 120 is fully seated with a bottom surface of the ring 122 against an outer surface of the bone 10, the fastener 112 may be inserted through the opening 126 in the ring 122. The fastener 112 may be driven into the vertebral body 10 through the center of the staple 120. This process is repeated for all desired levels. Once the fastener systems 110 are placed, the cord 140 may be selected and cut to length. The cord 140 is positioned within the head portions 116 of each fastener 112. After the cord 140 is positioned within the head portion 116 of the fastener 112, the locking cap 130 may be positioned within the opening 106 such that the outer portion 132 is non-threadedly locked to the head portion 116 (e.g., rotated 90 degrees). This allows the cord 140 to be captured within the head portion 116 but still able to be tensioned. After final tensioning of the cord 140 is achieved, the inner portion 134 of the locking cap 130 may be rotated and threaded downwardly to contact and secure the cord 140 in its final position.

Turning now to FIGS. 3-6, an instrument 200 for tensioning a cord, for example, the cord 140 in system 100, according to one embodiment will be described. The instrument 200 may be configured to compress the spine during a thoracoscopic or open anterior spinal deformity correction procedure, for example. The instrument 200 may work with either a fusion or non-fusion procedure. It may be ineffective to compress the spine by manipulating minimally invasive surgical (MIS) tubes outside the wound because the tubes tend to flex. Instead, instrument 200 may be used in order to compress at the level of the respective fasteners 112. Furthermore, the instrument 200 is able to fit within a round, tubular port (e.g., 15 mm diameter) which is placed in the space between adjacent ribs. The instrument 200 can exert a suitable amount of compression on the spine, for example, approximately up to 440 N [100 lbf] maximum.

Figure 7:
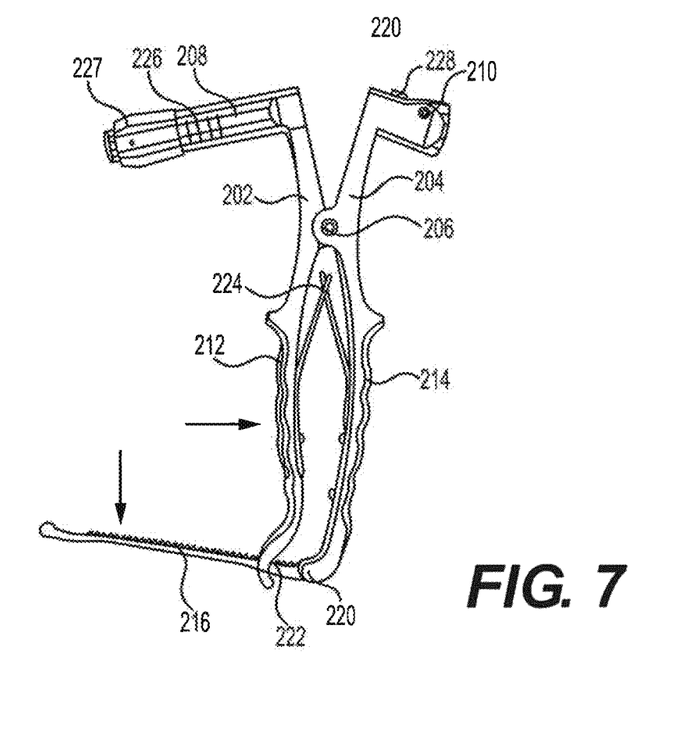
FIG. 7 is a compressed view of the instrument of FIG. 6 to tension the cord within the spinal system of FIG. 1.

The instrument 200 may include a first portion 202 and a second portion 204 coupled to the first portion 202 at a pivot point 206. The pivot point 206 may be provided by a pivot pin or other suitable mechanism to allow for pivotally connecting the first and second portions 202, 204 together. The first portion 202 includes a first tubular member 208 and the second portion 204 include a second tubular member 210. In a first position (e.g., shown in FIG. 3), the first and second tubular members 208, 210 are aligned along a common axis such that a central longitudinal opening extends therethrough. The first portion 202 defines a first handle portion 212 extending from the first tubular member 208 and the second portion 204 defines a second handle portion 214 extending from the second tubular member 210. In a second, compressed position (e.g., shown in FIG. 7), the first and second tubular members 208, 210 are not aligned along a common axis and are angled relative to one another.

The distal ends of the first and second handle portions 212, 214 may be connected with a ratchet 216. The ratchet may extend from the distal end of the second handle portion 214, for example, at a pivot 220, and engage with a pawl 222 on the first handle portion 212. When the first and second handle portions 212, 214 are squeezed towards one another, the pawl 222 can translate along teeth 218 on an upper surface of the ratchet 216 to maintain the first and second handle portions 212, 214 in the compressed configuration (e.g., shown in FIG. 7). The teeth 218 may be uni-directionally oriented to allow movement of the first handle 212 towards the second handle 214. The ratchet 216 may be disengaged from the pawl 222 to release the first handle portion 212 relative to the second handle portion 214. One or more springs 224 may be provided along inner surfaces of the handle portions 212, 214 to provide resistance to the instrument 200.

The first tubular member 208 may define a gauge sleeve 227 and a plurality of indicia 226. When the force gauge 227 moves, the plurality of indicia 226 may indicate the amount of compression force provided by the instrument 200. For example, the plurality of indicia 226 may be etchings provided, for example, in 100 N increments. The second tubular member 208 may retain a button 228 configured to unlock the shaft 234 and allow the cord 140 to move within the instrument 200.

Figures 4, 5:
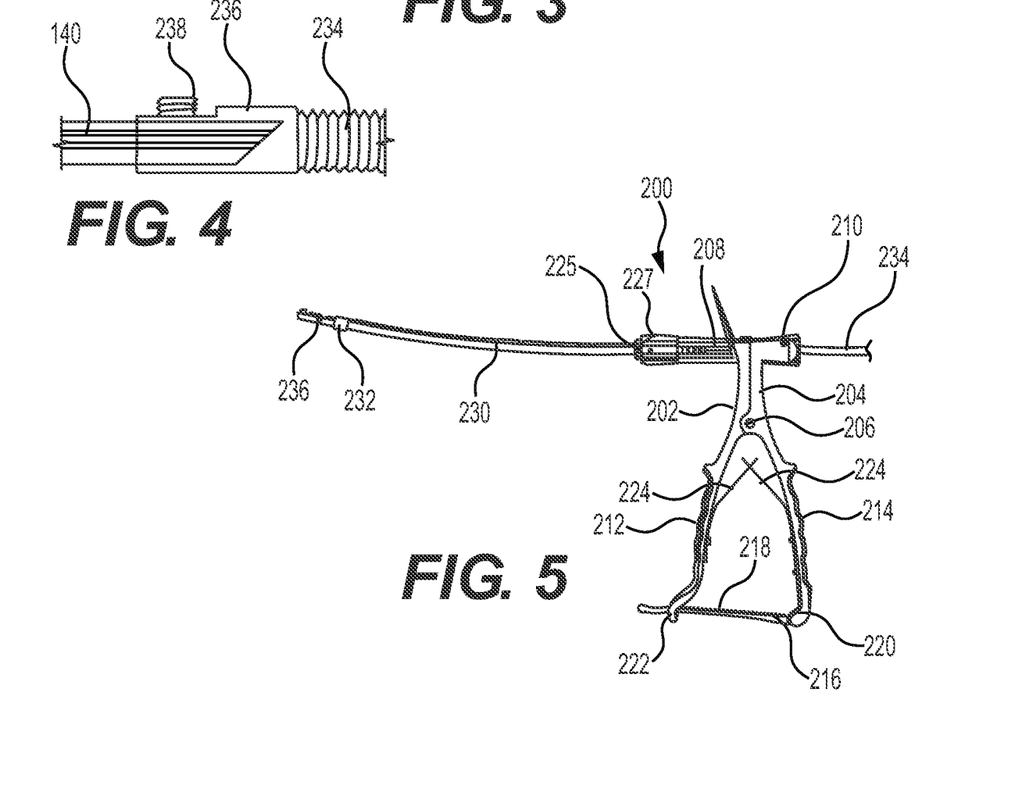
FIG. 4 is a close-up view of the cord attached to the threaded rod of the instrument in FIG. 3.
FIG. 5 is an assembled view of the instrument of FIG. 3.
Figure 6:
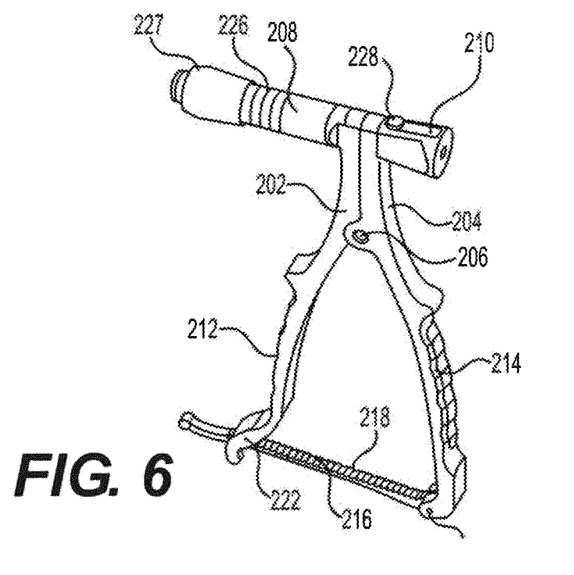
FIG. 6 is a perspective view of the instrument of FIG. 3 with the compressor tube and shaft removed for clarity.

In operation, a sleeve or compressor tube 230 is inserted into opening 225 in the first tubular member 208. A cap 232 may be place on the end of the compressor tube 230 opposite the end that was inserted into the instrument 200. The cap 232 may be, for example, a PEEK cap that is firmly secured to the end of the compressor tube 230. Next, a shaft 234 may be inserted into the open end of the tube 230. The shaft 234 may be a threaded shaft 234 that is threaded along a portion or the entire length of the shaft 234. The shaft 234 may be a flexible threaded rod, for example, constructed of polyetheretherketone (PEEK), polyoxymethylene (POM), or a similar flexible plastic. The threaded shaft 234 may have a chuck or collet 236 at one end. When the shaft 234 is inserted in the compressor tube 230, the end of the threaded shaft 234 and/or the collet 236 may be exposed beyond the end of the compressor tube 230 (e.g., as shown in FIG. 5). The button 228 may be depressed to slide the threaded shaft 234 through the first and second tubular members 208, 210.

As best seen in FIG. 4, the cord 140 may be inserted into an opening in the collet 236. The cord 140 may be secured to the collet 236, for example, with a fastener 238. The fastener 238 may be a threaded set screw or any other suitable mechanism for securing the cord 140 to the shaft 234. In the alternative, the collet 236 with the cord 140 previously connected thereto may be threaded onto the threaded shaft 234 to thereby secure the cord 140 to shaft 234.

The instrument 200 is operated by exerting a pull on the cord 140 relative to the sheath or tube 230 with the hand lever, as a result, the calipers or handles 212, 214 are compressed together. The rod or cord 140 may be attached to the flexible threaded rod 234 using the collet 236. The collet 236 may automatically grab the rod or cord 140 when pulled into the tube 230. It may be advantageous that both the flexible threaded rod 234 and tube 230 are pliable, thereby making it easier for the surgeon to guide the rod or cord 140 to a fastener 110 within the pleural space.

According to one embodiment, the procedure may follow the following sequence: (1) the patient may be placed in the lateral decubitus position with the convexity of the scoliotic curve facing up; (2) monoaxial pedicle screws 110 may be placed across the appropriate vertebral bodies, either through ports or through an open surgical exposure; (3) the compressor instrument 200 is assembled by pushing compressor tube 230 into the end and sliding flexible threaded rod 234 into the tube 230; (4) the rod (for fusion surgery) or cord 140 (for non-fusion surgery) is attached to collet 236 and pulled into the tube 230; (5) the tube 230 is inserted into the pleural space through either an incision or a port placed into an incision, which is placed caudally to the most caudal fastener 110; (6) the most cranial fastener 110 is located and the rod or cord 140 is placed into the yoke or head 116 of that screw and captured with a counter-torque; and the locking cap 130 of the fastener 1120 is tightened on the rod or cord 140; (7) the tube 230 is pulled back to expose more of the rod or cord 140, which is then placed into the yoke or head 116 of the adjacent (caudal) fastener 1120 and captured with the counter-torque; (8) the tube 230 is pushed forward until it abuts the counter torque; the compressor handles 212, 214 are squeezed until the desired compression force is achieved on the spine; and the locking cap 130 is fully tightened by threading the inner portion 134 of the locking cap 130 onto the cord 140; (9) steps 7 and 8 are repeated for the remainder of the screws 110; and (10) in the case where a rod has been implanted, the collet 236 is loosened and the compressor instrument 200 is removed from the pleural space; or in the case where a cord 140 has been implanted, the cord 140 may be cut with an electrocautery device, scalpel, scissors, or the like; and the compressor 200 is removed from the pleural space.

Figure 8:
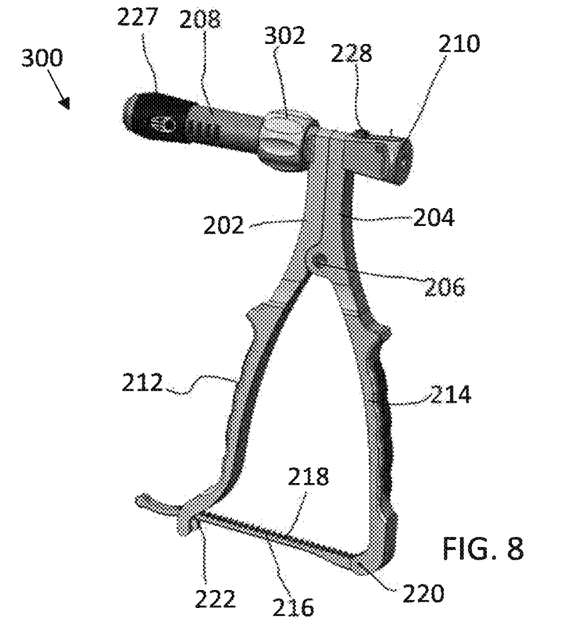
FIG. 8 is an alternative version of an instrument suitable for tensioning the cord according to another embodiment.

Turning now to FIG. 8, an alternative compression instrument 300, similar to instrument 200 will be described. Instrument 300 is similar in function to instrument 200 and like elements will be labeled with the same reference numbers. In addition to the features of instrument 200, instrument 300 provides a secondary method of applying compression to the construct. In this embodiment, the first and second tubular members 208, 210 may be additionally expanded apart by threads or another similar mechanism. The expansion of this fine-tuning mechanism increases the distance between the lock mechanism and the sheath or tube 230, applying force to the flexible rod 234, which holds the rod or cord 140. In particular, a thumb wheel 302 with threads configured to engage the threads of the threaded shaft 234 may provide finer control of the amount of compression applied to the rod or cord 140. In conjunction with the squeeze handles 212, 214, instrument 300 enables two stages of compression for both increased force application and finer control of applied force. In other words, handles 212, 214 provide for large amounts of compression and thumb wheel 302 provides for small amounts of compression, thereby allowing the surgeon to pinpoint a precise amount of compression on the rod or cord 140.

Figure 9:
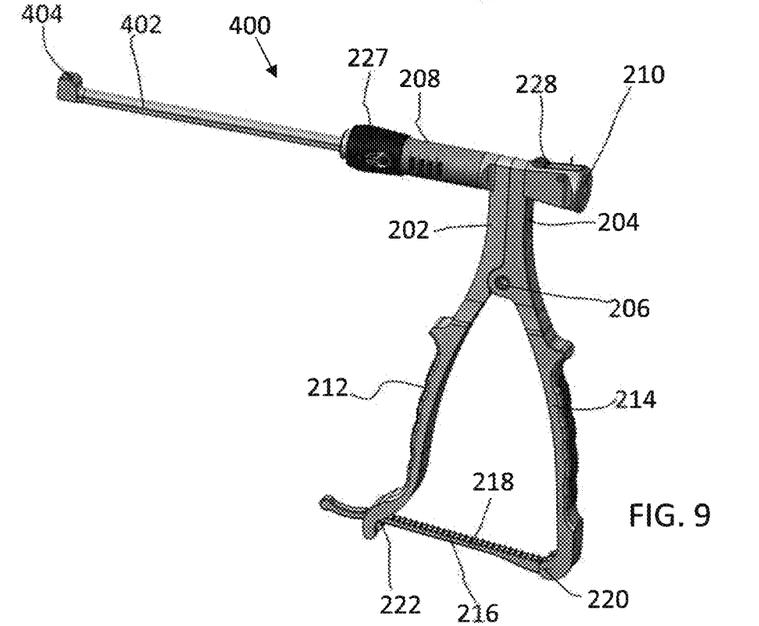
FIG. 9 is another version of an instrument suitable for tensioning the cord according to another embodiment.
Figure 10:
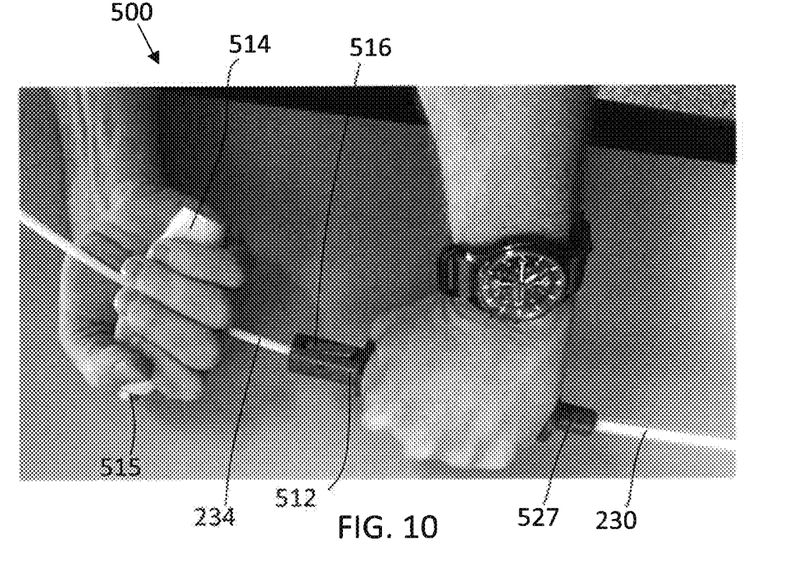
FIGS. 10-16 depict additional systems for tensioning the cord according other embodiments.
Figure 11:
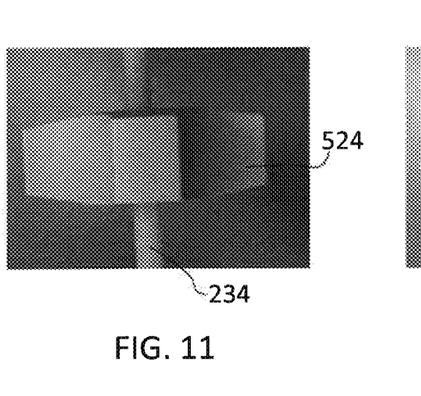

Turning now to FIG. 9, an alternative compression instrument 400, similar to instrument 200 will be described. Instrument 400 is similar in function to instrument 200 and like elements will be labeled with the same reference numbers. In instrument 400, the flexible tube 230 has been replaced with a rigid shaft 402. The rigid shaft 402 interfaces with the force gauge 227 at the proximal end. The rigid shaft 402 has a smooth channel or cannula which guides the rod or cord 140 and the flexible shaft 234 therein. At the distal tip 404 of the shaft 402, the channel may be curved, for example, to redirect the path of the captured rod or cord 140, allowing compression to be applied at an angle or perpendicular to the axial force on the construct.

Figure 12:
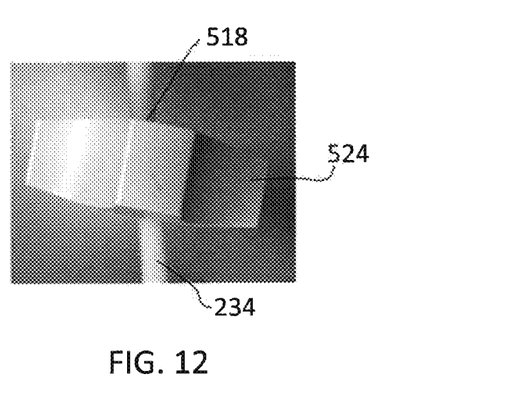
Figure 13:
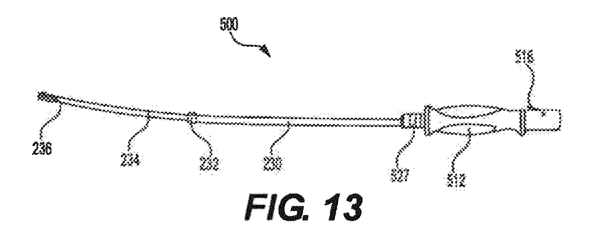
Figure 14:
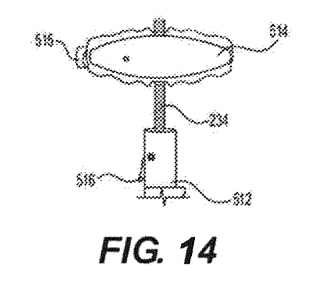
Figure 15:
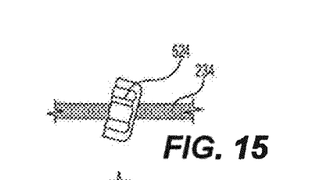
Figure 16:
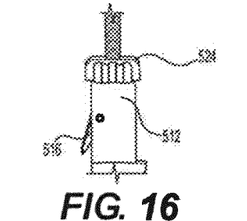

Turning now to FIGS. 10-16, alternative compression instruments 500 are shown. The compressor 500 may function in a manner similar to instrument 200, however, instead of squeeze handles 212, 214, the surgeon may hold two separate handles 512, 514 (one in each hand) and pulls them apart from one another to impart the compressive forces on the rod or cord 140. The main handle 512 grasps the compressor tube 230 and includes a ratcheting mechanism 516 and a force gauge 527. The other handle 514, may be in the form of a T-handle, for example, and may have a release button 515 so that it can be easily moved to a comfortable position on the flexible threaded shaft 234. This embodiment may be a good option for applying small compression forces to the spine. As an alternative to the T-handle 514, a knob 524 may be used. The knob 524 may have an internal thread and works like a nut when threaded onto the flexible shaft 234. To facilitate quick movement of the knob 524 along the threaded shaft 234, an off-axis through hole 518 may be drilled through the center of the knob 524, for example. When the knob 524 is tilted (canted), for example, as shown in FIGS. 12 and 15, then the internal threads are disengaged and the knob 524 can be rapidly pushed or pulled along the flexible shaft 234. For example, the knob 524 may be moved along shaft 234 until it abuts the main handle 512, for example, as shown in FIG. 16. Once the knob 524 contacts the main handle 512, the knob 524 can be re-aligned to be coaxial with the flexible shaft 234 and turned to apply compressive force to the spine. The inline handle 514 or knob 524 may tension the cord 140 between the final tightened screw and the most caudal screw. The compressive force, as indicated by the gauge 527 may be up to 150 N of compressive force (e.g., indicated in 50 N increments).

The embodiments described herein can provide large compressive, corrective forces and/or small fine-tuned corrective forces to be placed on the spine, for example, in a minimally invasive surgery. The forces may be exerted directly on the fasteners as opposed to indirectly exerting force on a long, flexible instrument attached to the screws. This allows the surgeon to control the force placed on the spine by offering force feedback to the surgeon in the form of the force gauge. The allows simplified placement of the cord into the yoke or head portion of an adjacent pedicle screw by simply pivoting the instrument relative to an already tightened pedicle screw. These systems can facilitate scoliosis correction and serve as a means for deformity correction with or without fusion.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A method of performing a spinal deformity correction for a plurality of vertebral bodies comprising:
    inserting into each one of a plurality of vertebral bodies a staple having a ring and a plurality of prongs extending downwardly from the ring for engaging bone;
    for each staple, inserting through the staple a threaded shaft of a bone screw into a respective vertebral body, each bone screw having a threaded head extending upwardly from the threaded shaft;
    placing a flexible tensioning line in a flexible tube extending from a tensioner having a pair of handles, wherein the flexible tensioning line includes a flexible cord to be placed in the threaded heads of the inserted bone screws and a flexible threaded shaft coupled to the cord, and placing a flexible tensioning line in a flexible tube comprises inserting the flexible threaded shaft into the flexible tube;
    for one of the inserted bone screw, placing the distal end of the flexible tube near the one inserted bone screw;
    squeezing the handles of the tensioner towards each other to apply a compressive force to the flexible tensioning line until an appropriate tensioning force is achieved;
    when the appropriate tensioning force is achieved, tightening a threaded locking cap in the threaded head of the one inserted bone screw to lock the flexible tensioning line to the one inserted bone screw.

2. The method of claim 1, further comprising repeating the steps of placing the distal end of the flexible tube near the one inserted bone screw, squeezing the handles and inserting a threaded locking cap for each of the remaining inserted bone screws.

3. The method of claim 1, wherein the tensioner includes a tension release mechanism and after the threaded locking cap is tightened, activating the tension release mechanism.

4. The method of claim 1, wherein the tensioner includes a tension release button and after the threaded locking cap is inserted, activating the tension release button to unlock the flexible tensioning line.

5. The method of claim 1, wherein the tensioner includes a plurality of force indicia and a movable force gauge such that when the tensioner handles are being squeezed, the force gauge moves along the plurality of indicia to indicate the force being applied by the tensioner.

6. The method of claim 1, wherein the tensioner includes a fine tuning thumbwheel that provides a fine tuning of the compressive force to the flexible tensioning line.

7. The method of claim 1, wherein the tensioner includes a ratcheting mechanism configured to apply a one-way compressive force to the flexible tensioning line.

8. The method of claim 7, wherein the ratcheting mechanism includes a pawl having a plurality of teeth and coupled between the two handles.

9. The method of claim 1, wherein the flexible tube includes an end cap at the distal end of the flexible tube.

10. The method of claim 9, wherein the end cap is made of PEEK material.

11. A method of performing a spinal deformity correction for a plurality of vertebral bodies comprising:
    providing a tensioner having a tubular body, a pair of handles coupled to the tubular body, a plurality of force indicia on the tubular body, a movable force gauge movable along the plurality of force indicia to indicate a force being applied by the tensioner;
    attaching a flexible tube to a distal end of the tubular body;
    on a convex side of the deformity, inserting into each one of a plurality of vertebral bodies a staple having a ring and a plurality of prongs extending downwardly from the ring for engaging bone;
    through the ring of each inserted staple, inserting a threaded shaft of a bone screw into a respective vertebral body, each bone screw having a threaded head extending upwardly from the threaded shaft;
    placing a flexible tensioning line in a flexible tube extending from a tensioner having a pair of handles, wherein the flexible tensioning line includes a flexible cord to be placed in the threaded heads of the inserted bone screws and a flexible threaded shaft coupled to the cord, and placing a flexible tensioning line in a flexible tube comprises inserting the flexible threaded shaft into the flexible tube
    for one of the inserted bone screw, placing the distal end of the flexible tube near the one inserted bone screw;
    squeezing the handles of the tensioner towards each other to apply a compressive force to the flexible tensioning line until an appropriate tensioning force is achieved;
    when the appropriate tensioning force is achieved, tightening a threaded locking cap in the threaded head of the one inserted bone screw to lock the flexible tensioning line to the one inserted bone screw.

12. The method of claim 11, wherein the tensioner includes a tension release mechanism and after the threaded locking cap is tightened, activating the tension release mechanism to release the tensioning force on the flexible tensioning line.

13. The method of claim 11, wherein the tensioner includes a fine tuning thumbwheel that provides a fine tuning of the compressive force to the flexible tensioning line.

14. The method of claim 11, wherein the tensioner includes a ratcheting mechanism configured to apply a one-way compressive force to the flexible tensioning line.

15. The method of claim 14, wherein the ratcheting mechanism includes a pawl having a plurality of teeth and coupled between the two handles.

16. The method of claim 15, wherein the flexible tube includes an end cap attached to the distal end of the flexible tube.

17. The method of claim 11, wherein the flexible tube includes an end cap at the distal end of the flexible tube.

18. The method of claim 17, wherein the end cap is made of PEEK material.

* * * * *